(12) United States Patent
Zabel et al.

(10) Patent No.: US 9,868,792 B2
(45) Date of Patent: Jan. 16, 2018

(54) METHODS OF ENHANCING ANTI-TUMOR IMMUNITY BY ADMINISTERING ANTIBODIES TO THE CCRL2 CHEMERIN RECEPTOR

(71) Applicant: The Board of Trustees of the Leland Stanford Junior University, Stanford, CA (US)

(72) Inventors: Brian A. Zabel, Redwood City, CA (US); Eugene C. Butcher, Portola Valley, CA (US); Russell K. Pachynski, Saint Louis, MO (US); Justin Monnier, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/199,476

(22) Filed: Jun. 30, 2016

(65) Prior Publication Data

US 2017/0002087 A1 Jan. 5, 2017

Related U.S. Application Data

(60) Provisional application No. 62/186,734, filed on Jun. 30, 2015.

(51) Int. Cl.
| | | |
|---|---|---|
| *C07K 16/30* | (2006.01) | |
| *A61K 39/395* | (2006.01) | |
| *A61K 45/06* | (2006.01) | |
| *A61K 9/00* | (2006.01) | |
| *A61K 39/00* | (2006.01) | |

(52) U.S. Cl.
CPC ............ *C07K 16/3053* (2013.01); *A61K 9/00* (2013.01); *A61K 39/39558* (2013.01); *A61K 45/06* (2013.01); *A61K 2039/505* (2013.01); *A61K 2039/507* (2013.01)

(58) Field of Classification Search
CPC .......... C07K 16/3053; A61K 39/39558; A61K 45/06; A61K 2039/505; A61K 2039/507
See application file for complete search history.

(56) References Cited

FOREIGN PATENT DOCUMENTS

WO WO2005005720 * 6/2005

OTHER PUBLICATIONS

Pachynski et al., "The chemoattractant chemerin suppresses melanoma by recruiting natural killer cell antitumor defenses", J Exp Med., Jul. 2, 2012, pp. 1427-1435, 209(8), The Rockefeller University Press, New York, NY.
Wittamer et al., "Specific Recruitment of Antigen-presenting Cells by Chemerin, a Novel Processed Ligand from Human Inflammatory Fluids", J Exp Med., Oct. 6, 2003, pp. 977-985, 198(7), The Rockefeller University Press, New York, NY.
Zabel et al., "Chemerin activation by serine proteases of the coagulation, fibrinolytic, and inflammatory cascades", . J Biol Chem., Oct. 14, 2005, pp. 34661-34666, 280(41), American Society for Biochemistry and Molecular Biology, Rockville, MD.
Zabel et al., Mast cell-expressed orphan receptor CCRL2 binds chemerin and is required for optimal induction of IgE-mediated passive cutaneous anaphylaxis:, J Exp Med., Sep. 15, 2008, pp. 2207-2220, 205(10), The Rockefeller University Press, New York, NY.
Monnier et al., "Expression, regulation, and function of atypical chemerin receptor CCRL2 on endothelial cells", J Immunol., Jun. 13, 2012, pp. 956-967, 189(2), The American Association of Immunologists, Inc., Rockville, MD.
Gonzalvo-Feo et al., "Endothelial cell-derived chemerin promotes dendritic cell transmigration", J Immunol., Mar. 1, 2014, pp. 2366-2373,192(5), The American Association of Immunologists, Inc., Rockville, MD.
Pachynski et al., "The chemoattractant chemerin suppresses melanoma by recruiting natural killer cell antitumor defenses", The Journal of experimental medicine, Jul. 2, 2012, pp. 1427-1435, 209(8), The Rockefeller University Press, New York, NY.
Del Prete et al., "CCRL2, a fringe member of the atypical chemoattractant receptor family", European journal of immunology, Jun. 2013, pp. 1418-1422, 43(6), John Wiley & Sons, Inc., Hoboken, NJ.
Mattern et al., "Processing, signaling, and physiological function of chemerin", IUBMB Life, Jan. 20, 2014, pp. 19-26, 66(1), John Wiley & Sons, Inc., Hoboken, NJ.
Zabel et al., "Chemerin regulation and role in host defense", Am J Clin Exp Immunol., Mar. 15, 2014, pp. 1-19, 3(1), e-Century Publishing Corporation, Madison, WI.
Monnier et al, "Expression, regulation, and function of atypical chemerin receptor CCRL2 on endothelial cells", Journal of immunology, Jul. 15, 2012, pp. 956-967, 189(2), The American Association of Immunologists, Inc., Rockville, MD.

* cited by examiner

*Primary Examiner* — Robert Landsman
(74) *Attorney, Agent, or Firm* — Pamela J. Sherwood; Bozicevic, Field & Francis LLP

(57) ABSTRACT

Chemerin is a chemoattractant that selectively directs intratumor recruitment of CMKLR1+ cells. Blockade of CCRL2 from binding to chemerin in non-neoplastic tumor cells, e.g. peri-tumor stromal and/or hematopoietic cells allows for redistribution of chemerin into the tumor and enhanced responsiveness against a tumor.

6 Claims, 7 Drawing Sheets
(7 of 7 Drawing Sheet(s) Filed in Color)

```
                       SEQUENCE LISTING

<160> NUMBER OF SEQ ID NOS: 1

<210> SEQ ID NO 1
<211> LENGTH: 25
<212> TYPE: PRT
<213> ORGANISM: Homo sapiens

<400> SEQUENCE: 1

Met Asp Asn Tyr Thr Val Ala Pro Asp Asp Glu Tyr Asp Val Leu Ile
 1               5                  10                  15

Leu Asp Asp Tyr Leu Asp Asn Ser Cys
            20                  25
```

METHODS OF ENHANCING ANTI-TUMOR IMMUNITY BY ADMINISTERING ANTIBODIES TO THE CCRL2 CHEMERIN RECEPTOR

CROSS REFERENCE

This application claims benefit of U.S. Provisional Patent Application No. 62/186,734, filed Jun. 30, 2015, now expired, this application is incorporated herein by reference in its entirety.

GOVERNMENT RIGHTS

This invention was made with Government support under contract W81XWH-11-1-0512 awarded by the Department of Defense and under contracts AI079320 and CA169354 awarded by the National Institutes of Health. The Government has certain rights in the invention.

BACKGROUND

Chemoattractants acting through their cognate receptors are critical for the recruitment of effector immune cells to inflamed tissues, and are therefore of considerable interest as potential targets for the treatment of inflammatory disease. CCRL2 (also known as HCR, CRAM-A and CRAM-B) encodes an orphan chemokine receptor-like protein, which is predicted to be a seven transmembrane protein. G protein coupled receptors (GPCRs) are a family of approximately 500 proteins with a 7 transmembrane structure that are involved in variety of biological functions.

For classical chemoattractant receptors, interaction with its cognate ligand causes a conformational change in the protein and facilitates the binding of small associated heterotrimeric G proteins to the intracellular receptor domains, which initiate a signaling cascade. 'Atypical' chemoattractant receptors bind to chemoattractants but do not transduce intracellular signals leading to cell migration. This functionally defined receptor subfamily is currently comprised of three members-D6, DARC (Duffy antigen receptor for chemokines), and CCX-CKR (Chemocentryx chemokine receptor). The receptors are also referred to as professional chemokine "interceptors", a name that reflects their ability to efficiently internalize bound ligand.

Despite recent advances, cancer continues to be a leading cause of mortality worldwide. Harnessing a patient's immune system to destroy cancer cells is a promising therapeutic strategy. However, most current cancer immunotherapies selectively activate a limited repertoire of immune defenses and often have incomplete efficacy. A major immune evasion strategy of cancer cells is the establishment of an immunosuppressive tumor microenvironment through the selective recruitment of M2 macrophages, myeloid-derived suppressor cells (MDSCs) and tolerogenic DCs, and the exclusion of anti-tumor immune cells such as natural killer (NK) cells, M1 macrophages and immunostimulatory DCs. However, the underlying cell trafficking mechanisms that govern this process are incompletely understood.

Chemerin is a chemoattractant that is downregulated in several cancers including melanoma, prostate, lung, breast and colon cancer. Chemerin is produced and released by hepatocytes, endothelial cells, fibroblasts, adipocytes, epithelial cells, platelets and chondrocytes. Upon proteolytic processing, chemerin is activated and binds the G-protein coupled receptor chemokine receptor-like 1 (CMKLR1), which is expressed on several immune cells, in particular NK cells.

A second chemerin-binding receptor, CC-chemokine receptor-like 2 (CCRL2) is primarily expressed on endothelial cells, activated macrophages, and mast cells. Unlike CMKLR1, CCRL2 does not internalize or trigger intracellular calcium mobilization upon binding chemerin. Instead, CCRL2 binds chemerin with high affinity and presents it on the cell surface. The present invention provides for a role of CCRL2 in cancer progression.

SUMMARY

Methods are provided for immune targeting of cancer by contacting an individual with an agent that blocks CCRL2, and prevents CCRL2 from sequestering chemerin. It is shown herein that CCRL2 expression by the non-neoplastic, stromal cells associated with a tumor reduces anti-cancer immune responses. The non-neoplastic cells may include peri-tumor fibroblasts and other connective tissue cells, hematopoietic cells; etc. Blocking CCRL2 activity increases the bioavailability of chemerin, resulting in an enhancement of anti-cancer activity by the host immune system. In some embodiments the agent binds to CCRL2 on the cell surface. In some embodiments the agent decreases expression of CCRL2 on targeted cells. In some embodiments the contacting is performed in vivo. Methods of administration include, without limitation, systemic administration, intra-tumoral administration, etc. Administration may be repeated as necessary for depletion of the cancer cell population.

The methods of the invention may be combined with administration of a second immunoregulatory agent that acts to enhance immune system killing of cancer cells, which agent(s) may include neoplasia specific antibodies; immune checkpoint inhibitors; agonists of immune costimulatory molecules; and the like. In some embodiments, an effective dose of chemerin is co-administered with the anti-CCRL2 agent. Immunoregulatory modulating agents include one or more of an agent that agonizes an immune costimulatory molecule, e.g. CD40, OX40, etc.; and/or (iii) an agent that antagonizes an immune inhibitory molecule, e.g. CTLA-4, PD1, PDL1, etc. In some embodiments, a combination of agents provides a synergistic effect relative to the administration of an anti-CCRL2 agent as a monotherapy.

In some embodiments the cancer is a melanoma. In other embodiments the cancer is a carcinoma, i.e. a cancer of epithelial origin. Carcinomas of interest may include, without limitation, breast cancer, bladder cancer, cervical cancer, colorectal cancer, squamous cell cancer, liver cancer, lung cancer, ovarian cancer and prostate cancer.

In some embodiments the expression of CCRL2 on neoplastic cells of a tumor is analyzed prior to treatment, where tumors selected for treatment have CCRL2 negative neoplastic cells.

BRIEF DESCRIPTION OF THE FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
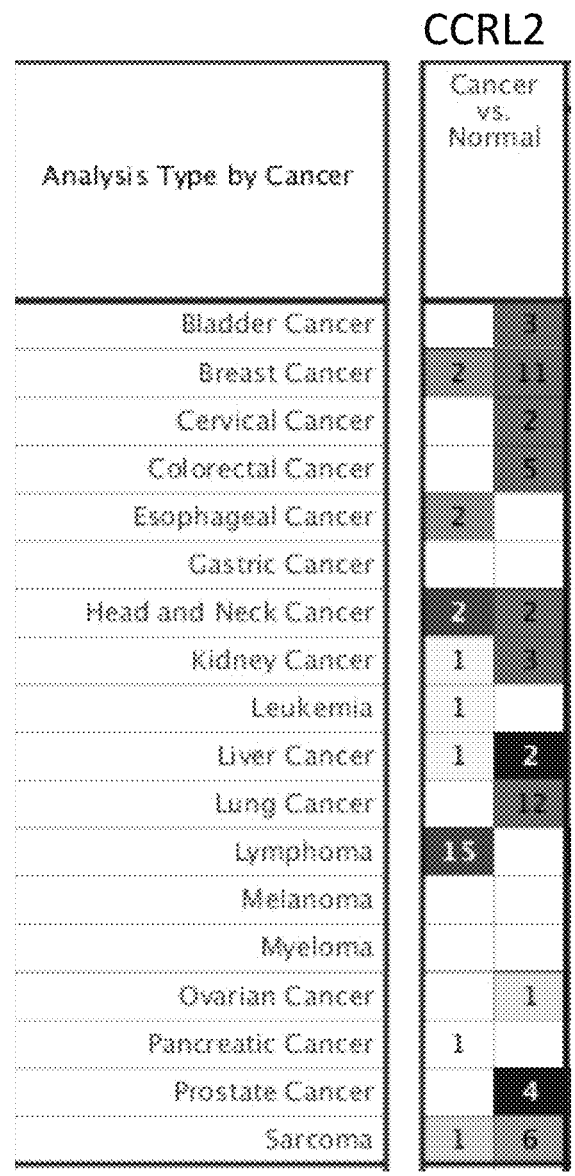
FIG. 1. Downregulation of CCRL2 in human epithelial cancer. Publically available datasets from Oncomine indicate that CCRL2 is downregulated in human cancers of epithelial origin. Blue=downregulation compared to normal tissue, red=upregulated; numbers in boxes indicate the number of datasets that demonstrate the indicate result. *$p<0.01$ by t-test.

Methods are provided for improving the immune response of an individual to cancer, where the cancer cells are contacted with an agent that blocks or otherwise downregulates CCRL2, e.g. CCRL2 in the tumor environment, e.g. peri-tumor non-neoplastic cells, stromal cells, peri-tumor macrophages, etc.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Anti-CCRL2 agent. CCRL2 is a chemokine receptor like protein, which is predicted to be a seven transmembrane protein and most closely related to CCR1. Chemokines and their receptors mediated signal transduction are critical for the recruitment of effector immune cells to the site of inflammation. It is expressed at high levels on activated macrophages, mast cells, and vascular endothelial cells.

CCRL2 was cloned as an orphan receptor and is known as human chemokine receptor (HCR), because it exhibits sequence homology to CC chemokine receptors (about 40% amino acid identity with CCR1, CCR2, CCR3, and CCR5). Two transcript variants of CCRL2 derived from alternative splicing have been described and named CCRL2A and CCRL2B. The deduced protein sequences for these variants differ only by the presence of 12 additional amino acids at the N-terminus in CCRL2A. CCRL2 binds, in the absence of any detectable signaling, chemerin, a chemotactic protein originally described as the agonist of two GPCRs: ChemR23/CMKLR1 and GPR1.

CCRL2 expression has been detected in many lymphoid organs (spleen, lymph node, fetal liver, bone marrow) as well as in nonlymphoid organs (heart and lung). Within the hematopoietic compartment, CCRL2 mRNA and protein have been reported in neutrophils, monocytes, dendritic cells (DCs), mast cells, NK cells, T cells, and CD34-positive cells. In general, CCRL2 is upregulated in activated cells. Constitutive CCRL2 RNA and protein expression has been detected in barrier cells such as bronchial epithelium and human endothelial cells and is upregulated during inflammatory conditions.

CCRL2 is believed to bind chemerin with high affinity such that the C-terminus of chemerin is available for interaction with cells expressing CMKLR1, a classically functioning chemerin receptor. CCRL2 is expressed under homeostatic and inflammatory conditions by human and mouse endothelial cells. Endothelial cells bind chemerin in the absence of ligand internalization, further supporting a role for CCRL2 in shaping the chemerin chemotactic gradient in vivo.

As used herein, the term "anti-CCRL2 agent" or "agent that provides for CCRL2 blockade" refers to any agent that reduces the binding of CCRL2 to chemerin. Non-limiting examples of suitable anti-CCRL2 reagents include antibodies that bind to CCRL2, anti-sense or RNAi agents that inhibit expression of CCRL2, small molecule inhibitors, and the like. In some embodiments, a suitable anti-CCRL2 agent (e.g. an anti-CCRL2 antibody) specifically binds CCRL2 to reduce the binding of CCRL2 to chemerin.

The efficacy of a suitable anti-CCRL2 agent can be assessed by assaying the agent. In an exemplary assay, target cells are contacted with candidate agent and in the presence of an effector cell, e.g. an immune effector cell, and the activity of the immune effector is determined. An agent for use in the methods of the invention will up-regulate neoplastic cell killing by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to killing in the absence of the agent.

Non-limiting examples of suitable antibodies that bind to human CCRL2 include antibodies described by Migeotte I, et al. 2002. Eur. J. Immunol. 32:494; and the anti-CCRL2 antibody 1B2 (available from AbCam), herein specifically incorporated by reference. Suitable anti-CCRL2 antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof. In some embodiments an anti-CCRL2 antibody comprises a human IgG Fc region, e.g. an IgG1, IgG2a, IgG2b, IgG3, IgG4 constant region.

The anti-CCRL2 agent may be an antisense oligonucleotide (ODN), particularly synthetic ODN having chemical modifications from native nucleic acids, or nucleic acid constructs that express such antisense molecules as RNA. The antisense sequence is complementary to the targeted RNA, and inhibits its expression. One or a combination of antisense molecules may be administered, where a combination may comprise multiple different sequences.

Antisense molecules may be produced by expression of all or a part of the target RNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5-O-phosphorothioate, 3'-CH2-5'-O-phosphonate and 3'-NH-5-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural.beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the CCRL2 RNA. By RNAi agent is meant an agent that modulates expression by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Immune Responsiveness Modulators. Immune checkpoint proteins are immune inhibitory molecules that act to decrease immune responsiveness toward a target cell, particularly against a neoplastic tumor cell in the methods of the invention. Endogenous responses to neoplastic cells by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness. In some embodiments, an in vitro assay of T cell activation is used in the determination of specific combinations and dosing schedules.

Tumor-associated antigens (TAAs) are relatively restricted to neoplastic tumor cells, whereas tumor-specific antigens (TSAs) are unique to neoplastic tumor cells. TSAs and TAAs typically are portions of intracellular molecules expressed on the cell surface as part of the major histocompatibility complex.

Tissue specific differentiation antigens are molecules present on neoplastic tumor cells and their normal cell counterparts. Tumor-associated antigens known to be recognized by therapeutic mAbs fall into several different categories. Hematopoietic differentiation antigens are glycoproteins that are usually associated with cluster of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA, epidermal growth factor receptor (EGFR; also known as ERBB1)' ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11). Antigens involved in angiogenesis are usually proteins or growth factors that support the formation of new microvasculature, including vascular endothelial growth factor (VEGF), VEGF receptor (VEGFR), integrin αVβ3 and integrin α5β1. Tumor stroma and the extracellular matrix are indispensable support structures for a tumor. Stromal and extracellular matrix antigens that are therapeutic targets include fibroblast activation protein (FAP) and tenascin.

Examples of useful therapeutic antibodies include, without limitation, rituximab; Ibritumomab; tiuxetan; tositumomab; Brentuximab; vedotin; Gemtuzumab; ozogamicin; Alemtuzumab; IGN101; adecatumumab; Labetuzumab;

huA33; Pemtumomab; oregovomab; CC49 (minretumomab); cG250; J591; MOv18; MORAb-003 (farletuzumab); 3F8, ch14.18; KW-2871; hu3S193; IgN311; Bevacizumab; IM-2C6; CDP791; Etaracizumab; Volociximab; Cetuximab, panitumumab, nimotuzumab; 806; Trastuzumab; pertuzumab; MM-121; AMG 102, METMAB; SCH 900105; AVE1642, IMC-A12, MK-0646, R1507; CP 751871; KB004; IIIA4; Mapatumumab (HGS-ETR1); HGS-ETR2; CS-1008; Denosumab; Sibrotuzumab; F19; and 81C6.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD1 are PD1 ligand 1 (PDL1; also known as B7-H1 and CD274) and PDL2 (also known as B7-DC and CD273). PDL1 is expressed on cancer cells and through binding to its receptor PD1 on T cells it inhibits T cell activation/function.

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages.

Anti CCR4 (CD194) antibodies of interest include humanized monoclonal antibodies directed against C-C chemokine receptor 4 (CCR4) with potential anti-inflammatory and antineoplastic activities. CCR2 is expressed on inflammatory macrophages that can be found in various inflammatory conditions, e.g. rheumatoid arthritis; and have also been identified as expressed on tumor promoting macrophages. CCR2 is also expressed on regulatory T cells, and the CCR2 ligand, CCL2, mediates recruitment of regulatory T cells into tumors. Regulatory T cells suppress a response for anti-tumor T cells and thus their inhibition or depletion is desired.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," or "neoplastic cells" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. In some embodiments the cancer is a melanoma. In other embodiments the cancer is a carcinoma, i.e. a cancer of epithelial origin. Carcinomas of interest may include, without limitation, breast cancer, bladder cancer, cervical cancer, colorectal cancer, squamous cell cancer, liver cancer, lung cancer, ovarian cancer and prostate cancer.

An important aspect of the present invention relates to non-neoplastic cells in or associated with a tumor. As is known in the art, although some neoplasias grow as cell suspensions, most grow as solid masses of tissue, which may be referred to as a tumor, or solid tumor. Solid tumors have a distinct structure that mimics that of normal tissues and comprises two distinct but interdependent compartments: the parenchyma (neoplastic cells) and the non-neoplastic stroma that the neoplastic cells induce and in which they are dispersed. All solid tumors have stroma and require stroma for nutritional support and for the removal of waste products. In solid tumors, stroma includes connective tissue, blood vessels, and, very often, inflammatory cells, all of which are interposed between the malignant cells and normal host tissues. In all tumors, stroma is largely a product of the host and is induced as the result of tumor cell-host interactions. Solid tumors, regardless of their type or cellular origin, require stroma if they are to grow beyond a minimal size of 1 to 2 mm. The stroma of solid tumors may also limit the influx of inflammatory cells or may limit the egress of tumor cells.

The major components of tumor stroma include, in addition to new blood vessels, leaked plasma and plasma proteins; proteoglycans and glycosaminoglycans; interstitial collagens (primarily types I and III); fibrin; fibronectin; and cells of two general types, normal connective tissue cells such as fibroblasts and hematopoietic or immune cells that are derived from the blood. Reference may be made herein to non-neoplastic cells of a tumor, which may include various stromal elements of a tumor, and associated hematopoietic cells.

CCRL2 blockade therapy can enhance the therapeutic response of an individual to antagonistic or agonistic immunotherapies by enhancing the stimulation of immune effector cells by chemerin. Thus, the anti-tumor efficacy of tumors that are responsive to these therapies is enhanced.

A combination of CCRL2 blockade, with an immune therapy described herein may be given to patients with cancer subtypes that are responsive to these therapies. These cancers may be defined by a higher frequency of mutations, resulting in more neoplastic antigens, therefore being more immunogenic, as described above. In some embodiments patients treated with combination therapy are responsive to treatment with an immune activator or checkpoint inhibitor. In other embodiments, patients are treated with combination therapy of the invention that are currently-non-responsive to immunotherapies but have cancer-subtypes that are known to be responsive.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Spread," occurs when the neoplastic cells of a tumor disseminate into local or distant tissues and organs; which process may include metastasis. "Tumor invasion" occurs when the neoplastic growth spread out locally to compromise the function of involved tissues by compression, destruction, or prevention of normal organ function.

As used herein, the term "metastasis" refers to the growth of a cancer in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a cancer in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a monoacid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Methods of Use

Methods are provided for treating or reducing disease, including primary or metastatic cancer in a regimen comprising contacting the targeted cells with an anti-CCRL2 agent. Such methods include administering to a subject in need of treatment a therapeutically effective amount or an effective dose of the agent, including without limitation combinations of the agent with a second immune-oncology agent, e.g. anti-tumor antibody, checkpoint inhibitor, etc., chemotherapeutic drug, radiation therapy, or surgery.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing cancer growth, metastasis or invasion of cancers including carcinomas, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of disease can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

Also within the scope of the invention are kits comprising the active agents and formulations thereof, of the invention and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Chemerin is a chemoattractant that selectively directs intra-tumor recruitment of CMKLR1+ cells. Since CCRL2 regulates the local and systemic distribution of chemerin and coordinates leukocyte recruitment and migration, we investigated the contribution of CCRL2 to tumorigenesis.

Material and Methods

Animals. CCRL2−/− mice were obtained from Lexicon (The Woodlands, Tex., USA) and backcrossed 9 generations on the C57Bl/6 background. WT C57Bl/6 mice were obtained from Jackson Laboratories (Sacramento, Calif., USA). Mice were maintained in our facilities at the VA Palo Alto Health Care Systems (VAPAHCS) Veterinary Medical Unit and used at ~8-12 weeks of age. All animal experiments were conducted in accordance with approved VAPAHCS and National Institutes of Health Institutional Animal Care and Use Committee guidelines.

Reagents. Flow Cytometry Primary Antibodies. Anti-mouse antibodies: α-mCCRL2 (clone BZ2E3,), rat IgG2a isotype control (clone 9B5, generated in-house). α-mCMKLR1 (clone BZ186, generated in-house, mIgG1), α-mGPR1 (clone BZ48, generated in-house, rat IgG2a, mChemerin-hFc (generated in collaboration with Lake-Pharma). Anti-mCD31 were purchased from Biolegend (San Diego, Calif., USA), anti-CD3, anti-Ly6G, anti-DX5, anti-CD19-anti-CD4, anti-CD8, anti-GR1, anti-CD11 b, anti-CD11c, anti-F4/80, anti-CD 206, anti-CD45 and anti-MHCII were purchased from eBioscience (San Diego, Calif., USA).

Generating the anti-mCCRL2 mAbs BZ5B8 and BZ2E3. The immunizing amino-terminal mCCRL2 peptide with the sequence (SEQ ID NO:1) $NH_2$-MDNYTVAPDDEYDV-LILDDYLDNSC-COOH (corresponding to residues 1 -24 of mCCRL2, with a nonnative carboxyl-terminal cysteine to facilitate conjugation to keyhole limpet hemocyanin [KLH]) was synthesized by the Stanford Protein and Nucleic Acid Biotechnology Facility and conjugated to KLH according to the manufacturer's specifications (Thermo Fisher Scientific). Wistar Furth rats were immunized with the mCCRL2 peptide/KLH conjugate, first emulsified in CFA and then, subsequently, in IFA. Hybridomas producing anti-mCCRL2 mAbs were subcloned, and specificity was confirmed by reactivity with mCCRL2 but not other L1.2 receptor transfectants. An ELISA-based assay (BD Biosciences) was used to assess the $IgG_{2a}$ isotypes of the resulting rat anti-mouse CCRL2 mAbs, designated BZ5B8 and BZ2E3.

Flow Cytometry Anti-Secondary Antibodies. Goat anti-rat IgG-PE (R&D Systems, Minneapolis, Minn., USA), goat anti-human IgG-PE, rat anti-mouse-IgG PE (Invitrogen, Carlsbad, Calif., USA), B16-melanoma tumor model. Murine B16F0 melanoma, were obtained from the American Type Culture Collection. Cell lines were grown in complete media consisting of RPMI 1640 supplemented with 10% FBS, sodium pyruvate, penicillin/streptomycin, and β-mercaptoethanol. Melanoma tumor cells harvested from the same flasks were blindly inoculated subcutaneously at $0.5 \times 10^6$ cells per mouse into WT or CCRL2–/– mice. Tumor growth was measured blindly every 2-4 days by calipers, and size was expressed as the product of perpendicular length by width in square millimeters (9). Mice were euthanized when tumor size reached~400 $mm^2$ or when tumor sites ulcerated.

Tumor Leukocyte Isolation. At indicated time points, mice were euthanized and the tumor was surgically excised from the skin. After removal of adjacent dermal layers, B16 melanomas were weighed, and then mechanically crushed in a 50 ml falcon tube using a 5 ml syringe. Crushed melanomas were then re-suspended with 5 ml of collagenase 4 (5 mg/ml) and incubated in a shaker at 37C for 30 min. The collagenase digested melanoma was then passed over a 40 μn cell strainer, and was washed several times with cold PBS. Cells were then centrifuged for 3 min at 1500 RPM, and the supernatant discarded. Cells were re-suspended in 2 ml FACS buffer (PBS/2% FCS), and 100 μl of re-suspended cells was used for FACS analysis.

Flow Cytometry. For unconjugated antibodies (αCCRL2-2E3, αCMKLR1-186, αGPR1-43, mChem-hFc), cells were incubated with the indicated primary antibodies at 4° C. for 30 min in 100 μl of PBS/FBS 2% (Fetal Bovine Serum)/2% species specific serum. Cells were then washed with PBS and centrifuged for 3 min at 2000 rpm. Following the washing step, cells were incubated with PE conjugated secondary antibody 100 μl of PBS/2% FBS/2% goat serum. For directly conjugated antibodies: cells are incubated with labeled antibody at 4° C. for 30 min in 100 μl in PBS/2% FBS/2% species specific serum. Cells were washed and centrifuged for 3 min at 2000 rpm, re-suspended in 200 μl of PBS and were analyzed using a LSRII (BD Biosciences, Franklin Lake, N.J., USA). Before analyzing the stained cells by flow cytometery 1 μl of propidium iodide (PI) was added to the cells to exclude un-specific dead cell related fluorescent signal. Post-analysis of the data obtained by flow cytometry was performed using the FACS analysis software Flo-Jo.

Immunohistochemistry. On indicated time points, B16 melanoma tumors were surgically removed from the mouse skin, embedded in OCT, and frozen at –20C. Sections of frozen B16 melanoma cells of 10 μm thickness were cut using a cryostat, and placed on microscope slide (Company). Sections were left to air dry for 1h, after they which they were dipped in ice cold acetone for 20 min for fixation of the tissue. After another brief drying, sections were frozen at –20C until staining. Before staining, sections were thawed at room temperature and blocked with PBS/BSA 2% for 30 min at room temp. Primary antibodies, anti-CD31, anti-CD45, were incubated for 1 hour at RT in PBS/2% rat serum. After several washing steps in PBS, secondaries were added (alexa 488 or 554) for 30 min at room temp. After washing step, sections were counterstained with DAPI and mounted. Stained B16 melanoma sections were analyzed, and photographed using an inverted fluorescent microscope.

Image Analysis. Micro vessel Density Assessment. To evaluate micro-vessel density we first stained B16 tumor sections with CD31, a pan-endothelial cell marker, to visualize the tumor vasculature. CD31 stained tumor sections were then photographed using a fluorescent microscope suing 20× magnification. For each tumor section 5 pictures were taken at random areas of the tumors, and the number of CD31+ vessels were counted using PhotoShop (Adobe), and the data was graphed as number of vessel per high powered field.

B16 melanoma photography. Explanted B16 melanomas at day 16 were placed next to a same size indicator and photographed. Tumor photographs were then opened up in Photoshop, a scale bar of the same size was placed in all different melanoma pictures to maintain the proper scale between tumor sizes, and cropped sided by side to demonstrate the difference in size of B16 melanoma tumors between WT and CCRL2–/– mice.

Luminex. At day 10, B16 melanoma's were removed from WT and CCRL2–/– mice, and were weighed and 100 μl of PBS was added for every 100 mg of tumor weight. The tumors were then mechanically homogenized using an electric homogenizer. Tumor homogenates were then frozen at –20c until processed for Luminex. On the same day for each animal, ~500 ml of blood was collected via cardiac puncture using EDTA coated syringes, and plasma separation was performed by centrifuging the blood at 30000RPM for 10 min in EDTA coated microcentrigue tubes. Plasma and tumor homogenates were then transferred to Stanford's human immune monitoring core (HIMC) who ran the 38 cytokine panel Luminex assay.

Statistics. Evaluation of significance was performed using Student's t-test. Statistical tests were calculated using the Instat statistical program (Graphpad, La Jolla, Calif., USA), and graphs were plotted using Prism graphing software (Graphpad, La Jolla, Calif., USA). Data is expressed as mean±SD or SEM as indicated, and p– values less than 0.05 were considered to be significant.

Results

CCRL2 is downregulated in human epithelial tumors. We assessed expression of the gene encoding CCRL2 in publicly-available Oncomine datasets comparing patient tumors with their normal tissue counterparts. CCRL2 was significantly downregulated in tumors of epithelial origin (FIG. 1). The frequent down-regulation of both chemerin and chemerin receptor CCRL2 in malignant tumors suggests that chemerin expression by tumor cells or its retention by CCRL2 within the tumor might be deleterious to malignant cell survival or tumor progression. We hypothesized that CCRL2 expression by non-tumor stromal cells may sequester chemerin and restrict its access to tumor tissue. To test this hypothesis, we evaluated tumor progression in the well-characterized transplantable syngeneic B16F0 mouse melanoma model in WT and CCRL2-deficient mice.

Figure 3:
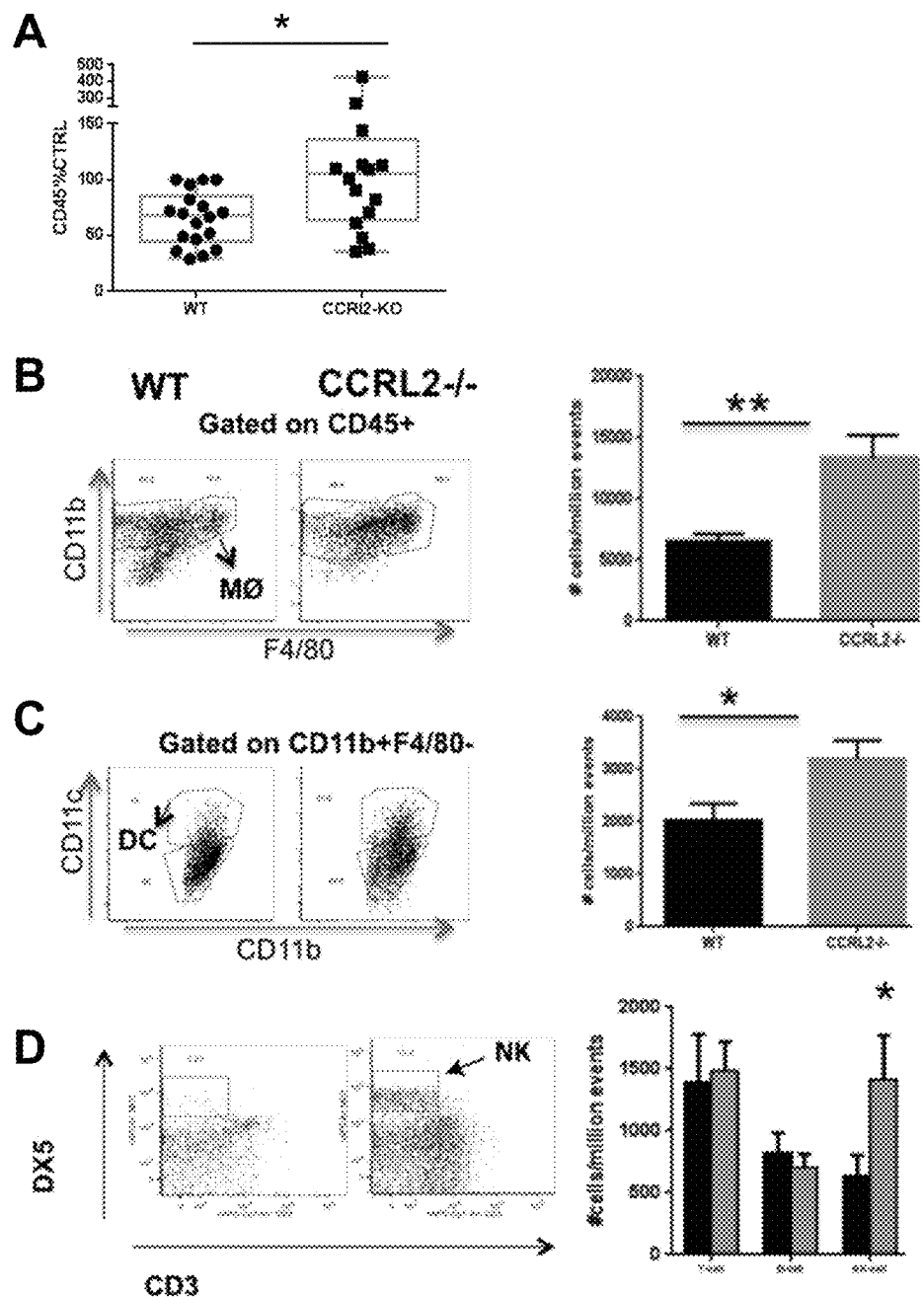
FIGS. 3A-3D. B16 melanoma tumors in CCRL2−/− mice have increased infiltrating CD45+leukocytes enriched in anti-tumor subsets. Leukocytes were extracted by enzymatic digestion from day 16 WT and CCRL2−/− mice B16 tumors and analyzed by flow cytometry. (A) 1 million cells were analyzed per tumor and dead cells were excluded by propidium iodide (PI) staining. Each data point represents the tumor infiltrating leukocytes (TIL) from an individual tumor, n=4 independent experiments. To combine mice from independent experiments, the number of CD45+ cells was normalized to the maximum value in WT mice in each experiment and expressed as percent of maximum. Mean ±range (lines)/SEM (grey boxes); n=16-18 different mice, *$p<0.05$ by t-test. Altered composition of TIL from CCRL2 KO mice: anti-tumor immune cells, including macrophages (CD11b+F4/80+) (B), immune stimulatory DCs (CD11b+F4/80-) (C), and NK cells (CD3-DXS+) (D) were enriched compared to the TIL of tumors from WT mice. There were no genotype-dependent differences in T or B cells. Mean±SEM; n=7 WT, n=5 CCRL2 KO mice. *$p<0.05$, **$p<0.01$ by t-test.
Figure 4:
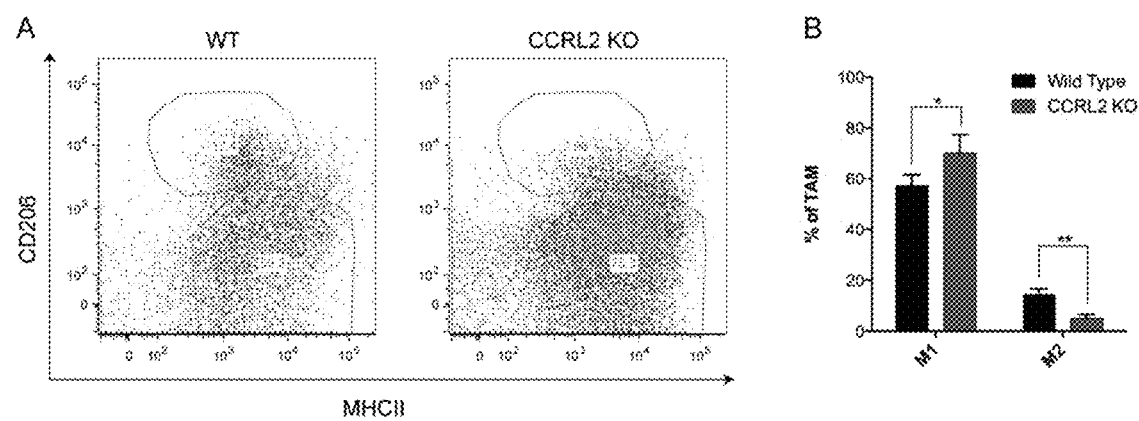
FIGS. 4A-4B. Shift in polarization of tumor-associated macrophages (TAM) to favor anti-tumor M1 immunophenotype in CCRL2 KO mice. Representative FACS plots of MHCII and CD206 staining on F4/80+ gated macrophages TAM in WT and CCRL2 KO mice (A). Quantification of M1 (MHCII+CD206-) and M2 (MHCII$^{low}$CD206+) polarized macrophages in WT and CCRL2 KO mice (B). Mean±SEM; *$p<0.05$, **$p<0.01$ by t-test.
Figure 5:
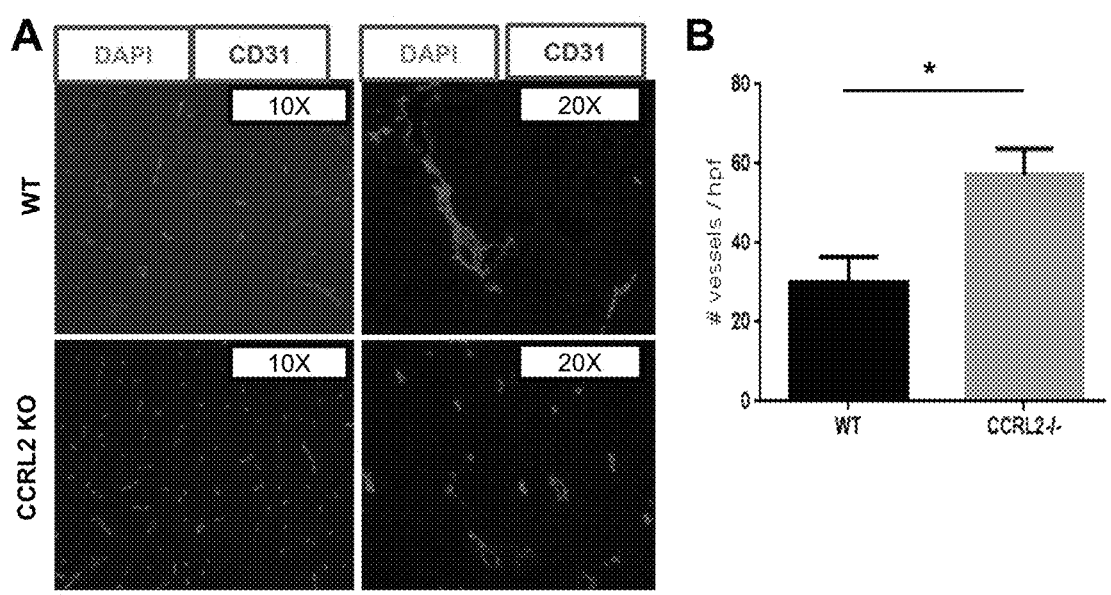
FIGS. 5A-5B: Increased micro-vessel density in B16 melanoma tumors in CCRL2−/− mice (A) On day 16, B16 melanoma were removed and processed for sectioning. Micro-vessel density was evaluated by immunofluorescence staining using the pan-endothelial cell marker CD31 (DAPI counterstain). Representative immunofluorescence images. (B) The number of CD31+ vessels from 5 images from each genotype were counted in blinded fashion. Mean±SEM of n=7-10 mice per genotype from 3 independent experiments; *$p<0.05$ by t-test.

Diminished melanoma tumor growth in CCRL2-deficient mice. B16 melanoma cells (0.5×10$^6$) were implanted subcutaneously in VVT and CCRL2$^{-/-}$ mice and tumor size was monitored over time. Tumor growth was significantly slower in CCRL2$^{-/-}$ mice compared with VVT (FIG. 1A), and tumor size at the conclusion of the study on day 16 was significantly reduced (by ~50%) in CCRL2$^{-/-}$ mice (FIG. 1B). The effect of CCRL2-deficiency on tumor growth was substantially greater than the effect of anti-CTLA4 antibodies, now FDA approved for melanoma therapy, when anti-CTLA4 antibodies were tested in the same pre-clinical model B16 melanoma tumors from CCRL2-deficient mice have more infiltrating anti-tumor leukocytes. CCRL2-deficiency enhanced the infiltration of leukocytes, which was associated with an increase in the relative representation of anti-tumor leukocytes. There was a significant increase in CD45$^+$ cells in dissociated cell suspensions of tumors from CCRL2 KO mice compared with controls (FIG. 3 A). On average, the frequency of anti-tumor immune cells, including macrophages (CD11b+F4/80+) (FIG. 3B), immune stimulatory DCs (CD11b+F4/80−) (FIG. 3C), and NK cells (CD3−DX5+)(FIG. 3D) were enriched compared to the tumor-infiltrating leukocytes of tumors from VVT mice. There were no genotype-dependent differences in the frequency of T or B lymphocytes. Furthermore, there was a shift in the polarization of tumor-associated macrophages to favor anti-tumor M1 (F4/80+MHC class II+CD206−) vs. immune suppressive M2 (F4/80+MHC class II$^{low}$CD206+) macrophages (FIG. 4). Shifts in the ratios of M1 to M2 can have a significant impact on tumor growth and may be important in the overall pro/antitumor balance of the local tumor microenvironment.

Figure 2:
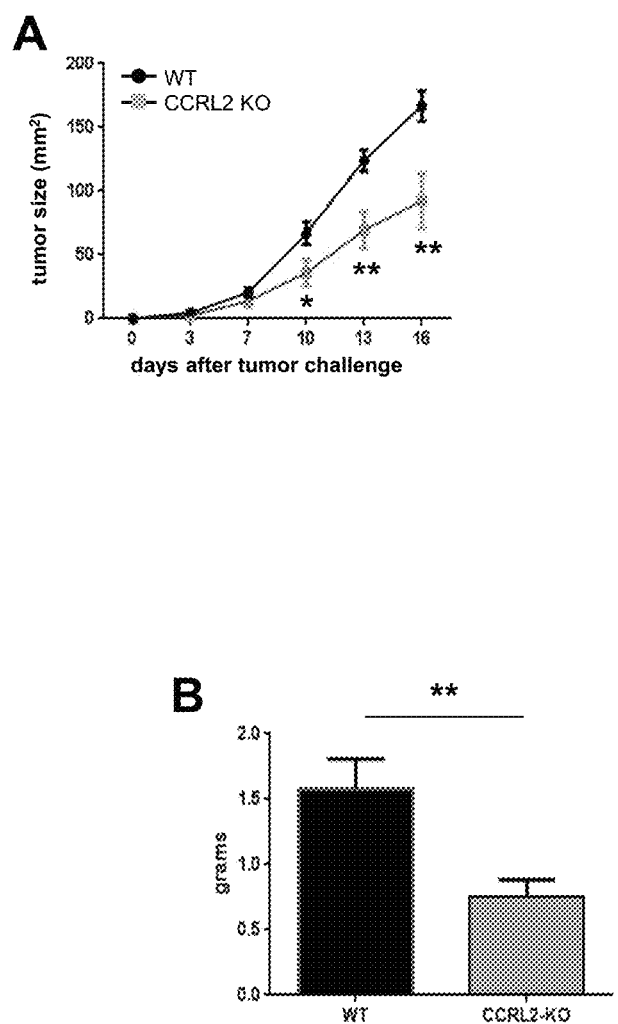
FIGS. 2A-2B. B16 melanoma growth is attenuated in CCRL2 deficient mice. B16 melanoma is a highly aggressive syngeneic, orthotopic melanoma cancer model that is relatively resistant to immune control. (A) Measure of tumor size in WT (black) and CCRL2 KO (green) mice over time. (B) Tumor weights after excision on day 16 post-implantation. Mean ±SEM; n=7 WT, n=5 CCRL2 KO mice; *$p<0.05$, **$p<0.01$ by t-test. Data is from one representative experiment of 4 with similar results.

B16 melanoma tumors from CCRL2-deficient mice have increased micro vessel density. Tumor vascularization is typically an important rate limiting determinant for tumor growth in solid tumors, and CCRL2 is expressed on vascular endothelial cells. Here we asked whether there was a difference in the vascularization of B16 tumors between VVT and CCRL2$^{-/-}$ mice that may underlie the genotype-dependent differences in tumor growth. We assessed tumor vascularization by staining frozen sections with pan-blood vessel marker CD31 and counting the number of labeled vessels per field. The CD31-defined blood vessels in tumors from CCRL2$^{-/-}$ mice appeared smaller in diameter than controls (FIG. 2A), and there were significantly more microvessels in tumors from CCRL2$^{-/-}$ mice tumors than VVT (FIG. 2B). The latter observation is somewhat surprising since increased vessel density is usually associated with increased tumor growth, however, in this case it may provide increased access for anti-tumor leukocytes.

Figure 6:
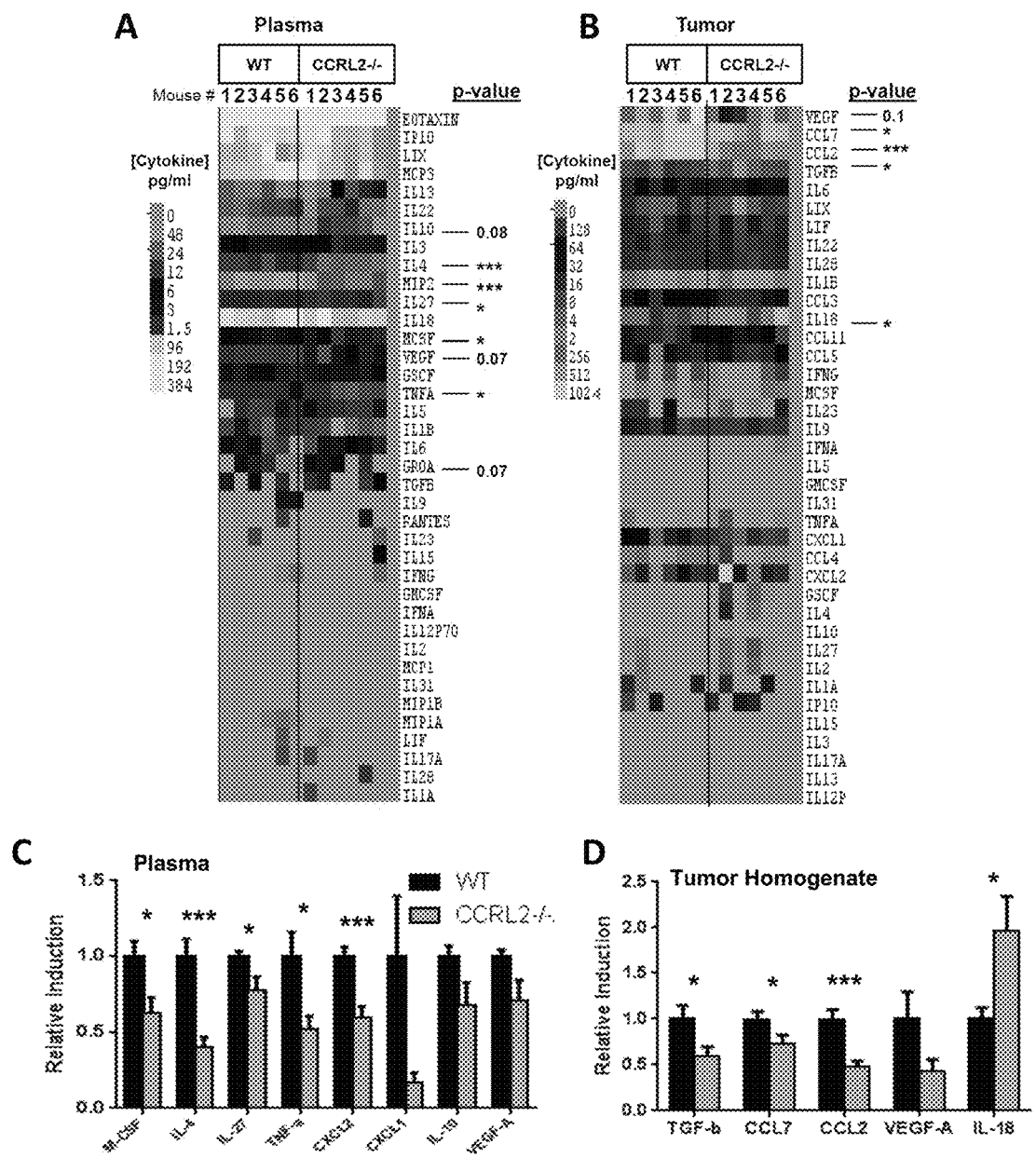
FIGS. 6A-6B. Plasma and tumor homogenate cytokine analysis from WT and CCRL2−/−melanoma-bearing mice. The abundance of a selected panel of cytokines, chemokines, and growth factors was measured by luminex in plasma and tumor homogenates from WT or CCRL2−/− B16 melanoma-bearing mice 10 days post-tumor implantation. (A, B) Heatmaps were generated using gene cluster 3.0 and by java tree view. (C, D) Raw analyte concentration data normalized and expressed relative to WT mice. Mean±SEM, n=6 mice/genotype. *$p<0.05$ t-test, ***$p<0.001$ t-test.

CCRL2-deficiency is associated with an anti-tumor cytokine profile. Cytokines, chemokines, and growth factors play a crucial role in the progression or inhibition of tumor growth. Here we asked if there were any genotype-dependent differences in selected secreted factors in plasma or tumor homogenates derived from tumor bearing CCRL2$^{-/-}$ and VVT mice. We measured 38 different cytokines and growth factors in both plasma and tumor homogenates at day 10 post-implantation by Luminex (FIG. 6). In the plasma of CCRL2$^{-/-}$ tumor bearing mice there was significantly less M-CSF, IL-4, IL-27, TNF-α, and CXCL2 (FIG. 6A,C). In the tumor homogenates from CCRL2$^{-/-}$ mice there was significantly less TGF-β, CCL7, CCL2, but significantly more IL-18 (FIG. 6B,D). Overall, the cytokine/chemokine/growth factor profile in plasma and tumor homogenates derived from tumor bearing CCRL2$^{-/-}$ mice was skewed toward an anti-tumor profile compared with WT.

Figure 7:
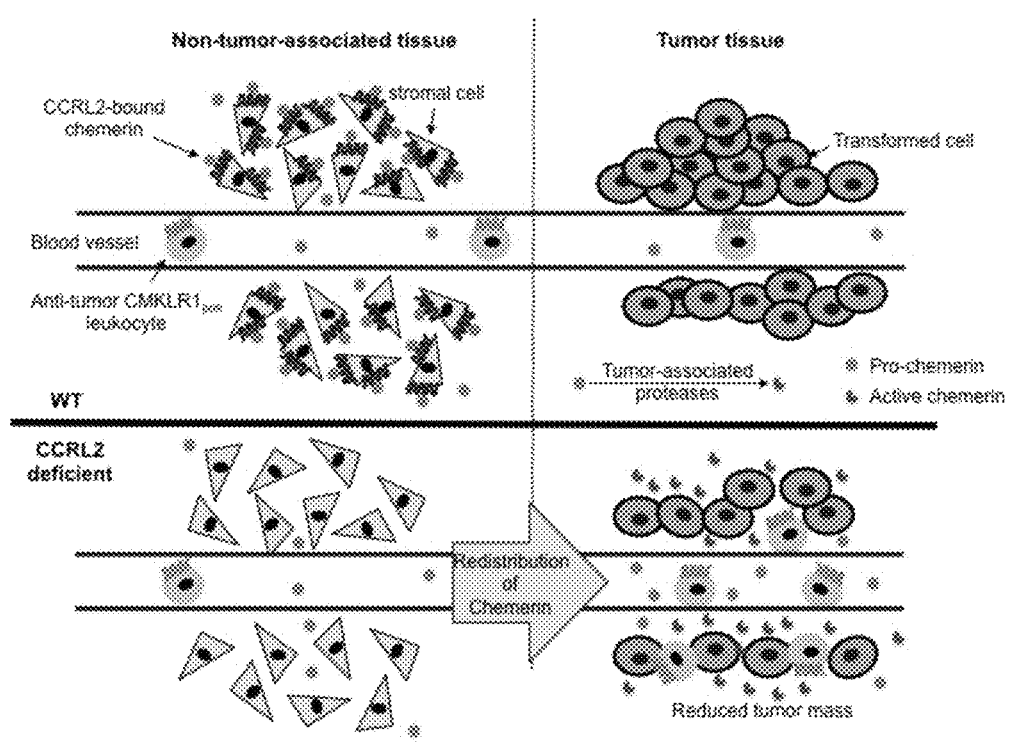
FIG. 7. Proposed model of chemerin-dependent anti-tumor CMKLR1+ leukocyte recruitment in CCRL2 KO mice. In WT mice, CCRL2 is expressed on non-tumor associated stromal cells such as lung endothelial cells or peri-tumor macrophages, where it prevents chemerin from reaching tumor tissues. In the absence of CCRL2, circulating pro-chemerin is redistributed to tumor tissue, where tumor-associated proteases activate it, causing CMKLR1+ leukocyte recruitment and tumor mass reduction.

Here we show for the first time a dramatic role for atypical chemerin receptor CCRL2 in controlling the progression of melanoma in preclinical tumor models. B16F0 melanoma cells implanted in mice deficient for CCRL2$^{-/-}$ mice form significantly smaller tumors than in VVT mice. This is associated with an increase in infiltrating CD45$^+$ leukocytes enriched in anti-tumor subsets including NK cells, immunostimulatory DC, and a shift in the polarization of tumor-associated macrophages to the M1 immunophenotype. We hypothesize that stromal cell-expressed CCRL2 normally acts by sequestering or redistributing chemerin away from the tumor, preventing NK and other CMKLR1+ anti-tumor cell recruitment (FIG. 7). The tumors from CCRL2$^{-/-}$ mice had higher micro-vessel density, perhaps enabling increased anti-tumor leukocyte access. The levels of cytokine/chemokine/growth factors in plasma and tumor homogenates from tumor bearing CCRL2$^{-/-}$ mice were skewed to favor an anti-tumor profile. The identification of CCRL2 as a major host inhibitor of chemerin-dependent anti-tumor immunity provides an opportunity to harness the effects of chemerin by antagonizing CCRL2.

While CCRL2 is downregulated in tumors of epithelial origin, CCRL2 appeared to be upregulated in human lymphoma (FIG. 1). This may reflect increased representation of activated CCRL2$^+$ macrophages in the lymphoma sample vs. normal lymph nodes, where CCRL2 signal is typically low.

Macrophage polarization (M1 pro-inflammatory or M2 immune suppressive) within the tumor micro-environment substantially affects the outcome of the anti-tumor response. For example, inducing M1 macrophage polarization by antagonizing CSF-1R was sufficient to induce potent anti-tumor response in in vivo models of glioblastoma multiforme. Hence, disruption of the M2 polarization pathway is sufficient to induce potent anti-tumor response.

TGF-β is one of the most immunosuppressive cytokines and has been clearly associated with inducing M2 polarization and tumor progression. CCL2 and CCL7 share a common receptor, CCR2, which has been clearly associated with cancer progression through the recruitment and survival of myeloid derived suppressor cells. VEGF-A is a well-known to promote cancer progression through stimulation of blood vessel development and tumor vascularization. Although VEGF-A was somewhat reduced in the tumor micro-environment, there were far more blood microvessels, which were smaller in diameter, in tumors from CCRL2−/− mice, and we did not note any difference in perfusion. It is controversial whether many smaller vessels vs. fewer large vessels correlates with increased angiogenesis and enhanced tumor growth. Finally, IL-18 has potent anti-tumor activity though activation of NK cells and cytotoxic T cells. Altogether, in tumors from CCRL2$^{-/-}$ mice there were reduced levels of tumor-promoting secreted factors (TGF-β, CCL2, CCL7 and VEGF-A) and higher levels of tumor inhibiting cytokine IL-18, which align with the cellular M1 pro-inflammatory macrophage environment.

Plasma cytokines follow a trend similar to the tumor homogenates, with significantly lower levels of M-CSF, IL-4, CXCL1, CXCL2, IL-10 and VEGF-A in tumor bearing CCRL2−/− mice. These secreted factors are associated with recruitment and survival of myeloid derived cells, M2 macrophage polarization, immune suppression and pathological angiogenesis. TNF-α has clear anti-tumor properties in melanoma and can trigger potent anti-melanoma responses in clinical settings, and is significantly lower in the plasma of CCRL2$^{−/−}$ mice.

In this preclinical melanoma study, the chemerin/CCRL2 pathway appears to be of the pro-inflammatory variety, where global genetic deficiency of CCRL2 results in a potent M1-associated anti-tumor response. The CCRL2 gene is conserved in humans and its cellular expression on endothelial cells and myeloid derived leukocytes is maintained in humans. Of particular interest is that CCRL2 is up-regulated on human dermal microvascular endothelial cells, and is highly expressed on a human CD34+ endothelial progenitors that incorporate in breast cancers.

Exploiting chemerin-dependent recruitment of immune cells into tumor tissues is a useful therapeutic strategy because it facilitates anti-tumor immune defenses independent of existing immunotherapeutics. Mobilizing endogenous immune defenses is a particularly exciting approach to pursue because of its potential to attract a broader and more cohesive repertoire of immune cells (e.g. NK cells, M1 macrophages, immune stimulatory DCs). In addition, by targeting a stromal cell-expressed antigen, anti-CCRL2 therapy could potentiate many existing cancer immunotherapies, which primarily target hematolymphoid cells. Ultimately these studies may lead to novel therapeutic strategies to treat neoplastic disease.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of enhancing immune response to an epithelial tumor in an individual wherein non-neoplastic cells express C-C chemokine receptor-like 2 (CCRL2), the method comprising:

administering a monoclonal antibody that reduces the binding of CCRL2 to chemerin and prevents CCRL2 from sequestering chemerin, in a dose effective to increase the bioavailability of chemerin, resulting in an enhancement of anti-cancer activity by the individual's immune system.

2. The method of claim 1, further comprising administering one or more of an agent that agonizes an immune costimulatory molecule and/or an agent that antagonizes an immune inhibitory molecule.

3. The method of claim 1, further comprising administering an antibody that binds to an antigen on the targeted tumor.

4. A method of enhancing immune response to melanoma in an individual wherein non-neoplastic cells express CCRL2, the method comprising:

administering a monoclonal antibody that reduces the binding of CCRL2 to chemerin and prevents CCRL2 from sequestering chemerin, in a dose effective to increase the bioavailability of chemerin, resulting in an enhancement of anti-cancer activity by the individual's immune system.

5. The method of claim 4, wherein the individual is a human.

6. The method of claim 4, further comprising co-administering an effective dose of chemerin with the monoclonal antibody.

* * * * *